United States Patent [19]

Roehl et al.

[11] 4,154,816

[45] May 15, 1979

[54] SOLID ANTIPERSPIRANT COMPOSITION AND PROCESS FOR ITS PREPARATION

[75] Inventors: Ernst-Ludwig Roehl; Hian-Bie Tan, both of Naarden, Netherlands

[73] Assignee: Naarden International N.V., Naarden-Bussum, Netherlands

[21] Appl. No.: 732,459

[22] Filed: Oct. 14, 1976

[30] Foreign Application Priority Data

Oct. 17, 1975 [NL] Netherlands ............... 7512239

[51] Int. Cl.$^2$ ............................................. A61K 7/38
[52] U.S. Cl. ............... 424/68; 424/DIG. 5; 424/65; 424/66; 424/67; 424/347
[58] Field of Search ............. 424/68, 66, DIG. 5

[56] References Cited

FOREIGN PATENT DOCUMENTS

| | | | |
|---|---|---|---|
| 2365219 | 7/1974 | Fed. Rep. of Germany | 424/68 |
| 2510364 | 9/1975 | Fed. Rep. of Germany | 424/68 |
| 1156812 | 7/1969 | United Kingdom | 424/68 |

OTHER PUBLICATIONS

Koichi et al., Chem. Abs., 1974, vol. 81, p. 153963p.
Masaaki et al., Chem. Abs., 1974, vol. 81, p. 137014z.
Kito, Chem. Abs., 1974, vol. 81, p. 106882b.

*Primary Examiner*—Dale R. Ore
*Attorney, Agent, or Firm*—Brumbaugh, Graves, Donohue & Raymond

[57] ABSTRACT

A solid, transparent, gelled antiperspirant composition containing one or more acidic reacting antiperspirant compounds wherein the gel contains a lower monohydric alcohol, a di- and/or trihydric alcohol and/or a lower polyglycol, a propylene-/ethyleneglycol-polycondensate, having the formula:

HO $(C_2H_4O)_x$ $(C_3H_6O)_y$ H, wherein $y/(x+y)=0.6-1$ and having an average molecular weight of at least 500, dibenzaldehyde-monosorbitol acetal, an antiperspirant metal compound, and mono- or dialkylolamide of a higher fatty acid.

9 Claims, No Drawings

SOLID ANTIPERSPIRANT COMPOSITION AND PROCESS FOR ITS PREPARATION

This invention relates to a means for preventing perspiration and a process for its preparation. More specifically the invention relates to such a means in solid state, e.g. a stick, with a transparent appearance.

Known antiperspirant sticks consist largely of gelled alcoholic solutions of antiperspirant compounds, the gelling agent being a sodium salt of a higher fatty acid like sodium stearate. However, such sticks cannot contain the usual antiperspirant compounds, because the acidic reaction of these compounds causes decomposition of the soap. To avoid this defect, alkaline reacting antiperspirant compounds were developed, like aluminum hydroxy chloride sodium lactate-complex, but they suffer from the disadvantage of having a poor antiperspirant effect. (see e.g. E. L. Roehl, Seifen, Öle, Fette, Wachse 99 (1973), no. 6/7 page 155 and P. Mannheim, Soap, Perfumery and Cosmetics 39 (1966), no. 10 page 807). On the other hand, antiperspirant sticks are known, containing the usual, acidic reacting antiperspirant compounds. These sticks are prepared from mixtures of solid and liquid waxes, but they lack the transparent appearance of a gelled stick that is so attractive to the consumer. Moreover these sticks are difficult to prepare, because often undesirable changes in shape occur on solidification of the warm liquid mass, after having been poured into the moulds.

It is therefore an object of the invention to provide a transparent, gelled, solid antiperspirant composition, e.g. in the shape of a stick, using efficient, acidic reacting antiperspirant compounds. The composition according to the invention is hydrophobic in character and thus brings on no irritation, even with persons having a very sensitive skin.

It was found that a solution of an acidic reacting antiperspirant compound in a mixture of monohydric alcohols with dihydric and/or trihydric alcohols and-/or lower polyglycols, can be gelled with dibenzaldehyde-monosorbitol acetal and a propyleneglycol/ethyleneglycol-polycondensate having the following formula: HO $(C_2H_4O)_x (C_3H_6O)_y$ H. This is surprising since it is known that dibenzaldehydemonosorbitol acetal is not stable in acidic media.

So the invention comprises a solid antiperspirant gel and a process for its preparation. The gel contains the following compounds in the amounts indicated (percentage by weight of the total compositon is given).

|  |  | preferably |
|---|---|---|
| Lower monohydric alcohols like ethanol and isopropanol | 10–80% | 20–50% |
| Di- and/or trihydric alcohols like propylene glycol and 1,3 butylene glycol and/or lower polyglycols | 10–60% | 20–40% |
| Propylene-/ethyleneglycol-polycondensate of the composition indicated | 5–30% | 10–20% |
| Dibenzaldehyde-mono-sorbitol acetal | 0,5–5% | 1–3% |
| Mono- or dialkylol-amides of higher fatty acids | 0–10% | 2–5% |
| Antiperspirant metal compounds | 4–15% | 2–6% |

The primarily hydrophobic polycondensate of propylene- and ethylene glycol has an average molecular weight of at least 500, preferably 1500–2500. The polycondensate contains enough propylene oxy units to ensure that x and y of the general formula HO $(C_2H_4O)_x (C_3H_6O)_y$ H have such values that $y/(x+y)$ lies between 0.6 and 1, preferably between 0.8 and 0.9.

The term "alkylolamides of higher fatty acids" is used to mean: "alkylolamides of fatty acids with 8–20 carbon atoms". Although the alkylolamides are not strictly necessary to obtain a satisfactory antiperspirant composition, they improve the stability, especially the odour stability of the composition. In particular the monoalkylolamides are doing very well in this respect.

The "lower polyglycols" may be condensation polymers of e.g. ethyleneglycol, 1,2-propyleneglycol or 1,3-butylene-glycol with an average molecular weight of at most 1100.

The antiperspirant metal compounds may be the usual compounds of aluminum, zinc and zirconium, especially aluminumhydroxy chlorides and bromides; aluminum hydroxy chlorides are prefered. These compounds may be added as a complex, e.g. with propyleneglycol.

The composition according to the invention may also be imparted a deodorant action by adding at most 2% of a suitable bactericide, e.g. a chlorophenol like hexachlorophene or 2,4,4'-trichloro-2'-hydroxydiphenylether.

To improve the attractiveness of the product to the consumer, up to 5% of a perfume may be added, as well as coloring if desired.

In preparing the composition according to the invention all compounds are mixed and heated to obtain a clear and homogeneous solution. This solution is subsequently poured into moulds and cooled.

The way and the sequence in which the components are mixed is not crucial. Preferably however, the antiperspirant metal compound is previously dissolved in part of the solvents (monohydric and/or polyhydric alcohols) and this solution is then added to the solution of the remaining components in the remainder of the solvents.

The example illustrates the preparation of a composition according to the invention but does not limit the scope thereof.

EXAMPLE 2 g. Dibenzaldehyde-monosorbitol acetal (e.g. Gell All-D of New Japan Chemical Co. Ltd., Osaka), 20 g. ethanol (96% by volume), 28.7 g. 1,2-propyleneglycol, 0.3 g. 2,4,4'-trichloro-2'-hydroxydiphenylether, 3 g. coconut-fatty-acid-mono-ethanolamide, 1 g. perfume and 15 g. ethyleneglycol/propyleneglycol-polycondensate are mixed and heated under reflux to obtain a clear and homogeneous solution. The polycondensate used has an average molecular weight of 1950 and contains 10% ethylene oxy units.

10 g. Rehydrol ASC (Reheis), an aluminum hydroxychloride-propyleneglycol-complex, is dissolved in 20 g. ethanol under reflux.

The clear solution thus obtained is added to the solution of the other cmponents. Again a clear solution is obtained with a temperature of 75–80° C. This solution is poured into moulds and cooled.

The solid antiperspirant composition thus obtained, showed excellent antiperspirant properties and stability and were very well tolerated by people who up till now could not use antiperspirants because of a sensitive skin.

We claim:

1. In a solid transparent gelled antiperspirant composition comprising (a) 10–80% by weight of a lower monohydric alcohol, (b) 10–60% by weight of a dihydric alcohol, a trihydric alcohol, a lower polyglycol, or a mixture of two or more thereof, (c) 2–15% by weight of acidic metal antiperspirant, (d) 0–10% by weight of a monoalkylolamide or dialkylolamide of a higher fatty acid, and (e) a gelling agent, the improvement wherein the gelling agent consists of 0.5 to 5% by weight of dibenzaldehyde-monosorbitol acetal and 5 to 30% by weight of a propylene-/ethylene glycol polycondensate having the formula $HO(C_2H_4O)_x(C_3H_6O)_yH$ wherein $y/(x+y)$ is 0.6 to 1, the polycondensate having an average molecular weight of at least 500.

2. The composition of claim 1 wherein said acetal is present in an amount of from 1 to 3% by weight, and said polycondensate is present in an amount of from 10 to 20% by weight.

3. The composition of claim 1 wherein said composition is a stick.

4. The composition of claim 1 further comprising up to 2% by weight of a bactericide and up to 5% by weight of a perfume.

5. The composition of claim 1 wherein (a), (b), (c) and (d) are present in the following amounts (a) 20–50% by weight of a lower monohydric alcohol, (b) 20–40% by weight of a dihydric alcohol, trihydric alcohol, a lower polyglycol, or a mixture of two or more thereof.

(c) 4–6% by weight of acidic metal antiperspirant, and (d) 2–5% by weight of a monoalkylolamide or dialkylolamide of a higher fatty acid.

6. The composition of claim 1 wherein (a) said polycondensate has a value for $y/(x+y)$ of between 0.8 to 0.9 and has an average molecular weight of 1500 to 2500, (b) said monohydric alcohol is selected from the group consisting of ethanol and isopropanol, (c) said dihydric alcohol is selected from the group consisting of propylene glycol and 1,3-butylene glycol, (d) said lower polyglycol has an average molecular weight of at most 1100 and is selected from the group consisting of condensation polymers of ethylene glycol, condensation polymers of 1,2-propylene glycol and condensation polymers of 1,3-butylene glycol, (e) said metal antiperspirant compound is selected from the group consisting of an aluminum hydroxy-chloride and an aluminum hydroxybromide, and (f) said monoalkylolamide or dialkylolamide is a monoalkylolamide or dialkylolamide of a higher fatty acid having 8–20 carbon atoms.

7. The composition of claim 6 further comprising up to 2% by weight of a bactericide, and up to 5% by weight of a perfume.

8. A process for preparing an improved solid transparent gelled antiperspirant composition comprising (a) 10–80% by weight of a lower monohydric alcohol, (b) 10–60% by weight of a dihydric alcohol, a trihydric alcohol, a lower polyglycol, or a mixture of two or more thereof, (c) 2–15% by weight of acidic metal antiperspirant, (d) 0–10% by weight of a mono-dialkylolamide or dialkylolamide of a higher fatty acid, and (e) a gelling agent, the improvement wherein the gelling agent consists of 0.5 to 5% by weight of dibenzaldehydemonosorbitol acetal and 5 to 30% by weight of a propylene-/ethylene glycol polycondensate having the formula $HO(C_2H_4O)_x(C_3H_6O)_yH$ wherein $y/(x+y)$ is 0.6 to 1, the polycondensate having an average molecular weight of at least 500, comprising mixing together said acetal, said polycondensate and said components (a), (b), (c) and (d), heating the mixture thus formed to obtain a clear and homogeneous solution, pouring said solution into molds, and cooling said molds.

9. A process according to claim 8 wherein said mixing step comprises forming a first solution of said component (c) in a portion of said component (a), in a portion of said component (b), or in a mixture of portions of said components (a) and (b), forming a second solution of said acetal, said polycondensate and component (d), and the portions of said components (a) and (b) which are not in said first solution, and mixing together said first and second solutions.

* * * * *

UNITED STATES PATENT AND TRADEMARK OFFICE
CERTIFICATE OF CORRECTION

PATENT NO. : 4,154,816
DATED : May 15, 1979
INVENTOR(S) : Ernst-Ludwig Roehl and Hian-Bie Tan It is certified that error appears in the above-identified patent and that said Letters Patent are hereby corrected as shown below:

First Page, Item [57], first line of ABSTRACT, after "solid", change the period to a comma;
Column 1, Line 62, "4-15% 2-6%" should read --2-15% 4-6%--;
Column 2, Line 59, "cmponents" should read --components--;
Column 4, Line 10, "8-20" should read --8 to 20--; and
Column 4, Line 22, "mono-dialkylolamide" should read --monoalkylolamide--.

Signed and Sealed this

Eleventh Day of September 1979

[SEAL]

Attest:

LUTRELLE F. PARKER
*Attesting Officer*   *Acting Commissioner of Patents and Trademarks*